United States Patent [19]

Wat

[11] 4,287,343

[45] Sep. 1, 1981

[54] PREPARATION OF N-CYANOIMIDATE HERBICIDE INTERMEDIATES

[75] Inventor: Edward K. W. Wat, Wilmington, Del.

[73] Assignee: E. I. Du Pont de Nemours and Company, Wilmington, Del.

[21] Appl. No.: 81,807

[22] Filed: Oct. 4, 1979

[51] Int. Cl.$^3$ ............... C07D 239/52; C07C 125/08; C07C 119/18; C07D 239/58
[52] U.S. Cl. ................................ 544/320; 564/106
[58] Field of Search .............. 260/551 C, 453 RW; 544/320

[56] References Cited

U.S. PATENT DOCUMENTS

| | | | |
|---|---|---|---|
| 2,697,727 | 12/1954 | Kaiser | 260/551 C |
| 2,971,973 | 2/1961 | Winthrop | 260/551 C |
| 3,225,077 | 12/1965 | Schaefer | 260/551 C |

Primary Examiner—Mark L. Berch

[57] ABSTRACT

Certain N-cyanoimidates are prepared by (a) contacting a propendimidate dihydrohalide salt with two equivalents of a base to produce a bisimidate; (b) contacting the bisimidate with cyanogen chloride to produce a mixture of N-cyanoimidate and a monohydrohalide bisimidate salt; (c) isolating the N-cyanoimidate. The N-cyanoimidate may, by heating, be converted to a pyrimidine, useful as a herbicide intermediate.

7 Claims, No Drawings

PREPARATION OF N-CYANOIMIDATE HERBICIDE INTERMEDIATES

BACKGROUND OF THE INVENTION

Coassigned application Ser. No. 840,389, filed Oct. 6, 1977, now U.S. Pat. No. 4,169,719, issued Oct. 2, 1979, described herbicidal sulfonamides prepared by reacting an appropriate 2-aminopyrimidine with an appropriately substituted sulfonyl isocyanate or isothiocyanate. The described sulfonamides are active herbicides and are especially useful in controlling nutsedge in crops such as cotton, corn, rice and wheat.

The development of an attractive process for preparing the above described sulfonamides by necessity involves finding inexpensive, easily employed processes for preparing the pyrimidine and isocyanate or isothiocyanate intermediates. The pyrimidine intermediate has been difficult to prepare due to hazards associated with raw materials and waste streams. Thus, any simplification in the preparation of the pyrimidine intermediate is desirable.

SUMMARY OF THE INVENTION

It has now been found that N-cyanoimidates of the formula

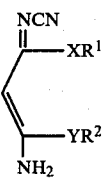

where
X and Y are independently oxygen or sulfur;
$R^1$ and $R^2$ are independently $C_1-C_4$ alkyl, $(CH_2)_nOR^3$, $CH_2CH_2Cl$ or $CH_2CF_3$;
$R^3$ is $C_1-C_4$ alkyl; and
n is 1 or 2;
provided that:
 (i) when $R^1$ is $CH_2CH_2Cl$ or $CH_2CF_3$, then X is 0, and
 (ii) when $R^2$ is $CH_2CH_2Cl$ or $CH_2CF_3$, then Y is 0;
may be prepared by a process comprising:
 (a) contacting a dihydrohalide salt of the formula:

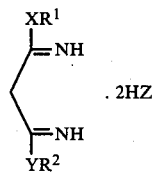

where X, Y, $R_1$ and $R^2$ are as defined above, and where Z is F, Cl or Br, with two equivalent weights of a base to produce a bisimidate; and
 (b) contacting the bisimidate with cyanogen chloride.

The N-cyanoimidates prepared in this manner are novel compounds claimed in coassigned U.S. application Ser. No. 840,389 now U.S. Pat. No. 4,169,719 and undergo ring closure on heating to yield pyrimidine intermediates.

DETAILED DESCRIPTION OF THE INVENTION

The process of this invention is summarized by the following flowchart:

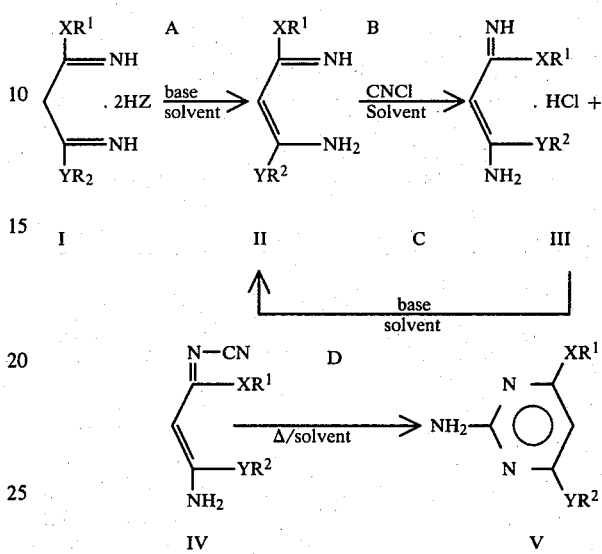

A dihydrohalide salt of Formula I, dimethyl 1,3-propanediimidate hydrochloride, is known in the art. Its synthesis is described in S. M. McElvain and J. P. Schroeder, JACS 71, 40 (1949) and in B. Harsteen, German Offenlegungsschrift No. 2,426,913, dated Dec. 11, 1975, the disclosures of which are herein incorporated by reference. Other compounds of Formula I can be prepared by the procedures described.

Reaction A involves the conversion of the dihydrohalide salt I to the bisimidate of Formula II. This is done by contacting, in an inert liquid medium the dihydrohalide salt with two mole equivalents of a base at a pH no lower than about 8. The base is preferably an alkali metal or alkaline earth carbonate or hydroxide and more preferably an alkali metal carbonate such as sodium or potassium carbonate.

Preferably, the salt I, which is suspended in an inert organic liquid medium, is added to an aqueous solution of the base. Suitable liquid mediums include chloroform and methylene chloride, the latter being preferred. The aqueous base to solvent ratio is preferably about 1:1 although higher or lower ratios are operable. The reaction mixture is cooled to maintain a temperature within the range of about $-10°$ to $+50°$ C., preferably in the range of about $-5°$ C. to $+5°$ C. The product bisimidate is contained in the organic phase.

Reaction A is exemplified by the following procedure: A suspension of I in one of the described liquid mediums is added to a solution or suspension of at least two equivalents of an aqueous base in ice-water. The organic phase containing the product II is removed and the water layer is further extracted with additional organic solvent. The combined organic solutions are dried over magnesium sulfate or sodium sulfate. If a different solvent is to be used in Reaction B, evaporation of solvent at reduced pressure yields an oily product.

In Reaction B, the bisimidate II is contacted with cyanogen chloride to prepare a mixture of the monohydrohalide salt III and the N-cyanoimidate IV. The reactants are combined in the organic layer retrieved from Reaction A, or, if the bisimidate has been isolated, in an inert organic solvent. Suitable solvents include methylene chloride, chloroform, tetrahydrofuran and dioxane, with methylene chloride being preferred. The cyanogen chloride is preferably in the amount of about one-half to about one mole per mole of bismidate. The reaction is run at a temperature of about 0° C. to 80° C., preferably about 20° C. to 45° C. When the solvent used is methylene chloride, pressure must be applied to achieve temperatures above reflux. The reaction time will vary with the temperature selected. For example, at the reflux temperature of methylene chloride, a reaction time of approximately 3 hours is required.

The monohydrohalide salt III precipitates during the reaction. Thus, the desired N-cyanoimidate IV may be isolated by filtration followed by evaporation of the solvent.

Reaction B is exemplified by the following procedure:

Gas or liquid cyanogen chloride is added to the solution of II prepared in Reaction A. Alternatively, solvent-free II is dissolved or suspended in an inert liquid medium to which cyanogen chloride is added. The mixture is heated, and a precipitate of monohydrohalide salt III is formed. The mixture is cooled to 25° C. and filtered. The filtrate contains the desired N-cyanoimidate IV which is isolated by evaporation of the solvent at reduced pressure. A solid residue remains which is further refined by washing with ether.

The monohydrohalide salt III may be recycled to produce the bisimidate II by following the procedure of Reaction A. Unlike Reaction A, however, only one equivalent of base is needed to neutralize the salt.

The bisimidates of Formula IV may be converted to herbicide intermediates of Formula V by heating. Preferably, the bisimidate is dissolved or suspended in a suitable inert liquid medium such as water, methanol, toluene or xylene and maintained at a temperature in the range of about 0° to about 200° C., preferably about 50° to about 150° C., until the rearrangement is complete. For lower boiling solvents, sufficient pressure is applied to achieve the desired reaction temperature. Alternatively, ring closure can be accomplished by heating the neat compound of Formula IV to a temperature above its melting point for a suitable period of time.

Reaction D is exemplified by the following procedures:

(1) A solution or suspension of IV in an inert liquid medium is heated to 65°–110° C. until rearrangement is complete (several hours at 65° C. to about 60 minutes at 110° C.); then the solution or suspension is cooled and the pyrimidine V is isolated by filtration or evaporation of the solvent;

(2) A compound of Formula IV is heated neat to its melting point. For example, when X and Y=0 and $R^1$ and $R^2$=methyl, heating to about 130° C. will give ring closure is less than one minute.

The ring closure of either procedure is highly exothermic and can lead to boiling of the liquid or a considerable rise in temperature of the melt when IV is heated neat. About cooling, V is isolated by filtration.

The pyrimidine of Formula V is reacted with a substituted sulfonyl isocyanate or isothiocyanate as described in the aforesaid U.S. Ser. No. 840,389, now U.S. Pat. No. 4,169,719 to produce an herbicidal sulfonamide. The disclosure of this patent is hereby incorporated by reference.

The process of this invention is further illustrated by the following example. Unless otherwise indicated, parts and percentage are by weight and temperatures are in degree centigrade.

EXAMPLE 1

Dimethyl-1,3-propendiimidate

To a stirred mixture of 400 ml aqueous potassium carbonate (300 g/liter) and 400 ml methylene chloride, 79 g of 1,3-propanediimidate dihydrochloride was added in portions. The organic layer was removed, and the aqueous layer was extracted with three-80 ml portions of methylene chloride. The combined organic layers were dried over anhydrous sodium sulfate and then filtered. The filtrate was evaporated to yield 51 g of a colorless liquid. This crude product was used in the next example without further purification.

EXAMPLE 2

Methyl 3-Amino-3-methoxy-N-cyano-2-propenimidate (a) A 3.5 ml portion of condensed cyanogen chloride was added to a solution of 8.4 g of the product of Example 1 in 100 ml tetrahydrofuran. The solution was stirred at 25° and a white solid began to form after ten minutes. After being stirred for 2 hours, the mixture was filtered. The solids were washed with tetrahydrofuran and dried to yield 4.5 g of a white solid, methyl 3-amino-3-methoxy-2-propenimidate hydrochloride, m.p. 72°–75°. The filtrate was evaporated at reduced pressure to give a solid residue containing a small amount of oil. A small volume of ether was added, and the mixture was filtered to give 3.6 g of methyl 3-amino-3-methoxy-N-cyano-2-propenimidate, m.p. 116°–121°. A second crop, 0.5 g, was obtained from the ether solution to give an overall yield of 41%. This yield may be increased by recycling the monohydrohalide salt.

(b) The procedure of part (a) was repeated using 25.5 g of the product of Example 1 in 150 ml methylene chloride and 10.1 ml cyanogen chloride. The mixture was refluxed for 3 hours. This reaction yielded 13.3 g of methyl 3-amino-3-methoxy-N-cyano-2-propenimidate and 12.2 g of methyl 3-amino-3-methoxy-2-propenimidate hydrochloride.

EXAMPLE 3

2-Amino-4,6-dimethoxypyrimidine

A mixture of 56.4 g of methyl 3-amino-3-methoxy-N-cyano-2-propenimidate in 200 ml toluene was refluxed for 4 hours. The resulting homogeneous solution was cooled to 0° and a solid precipitated. It was removed by filtration to yield 48.8 g of pale yellow solid, m.p. 92°–93.5°. A second crop of 5.2 g was obtained from the mother liquors for a total yield of 96%.

What is claimed is:

1. A process for preparing a pyrimidine compound of the formula

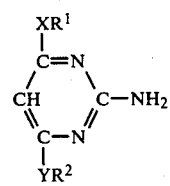

where

X and Y are independently oxygen or sulfur;
$R^1$ and $R^2$ are independently $C_1$-$C_4$ alkyl, $(CH_2)_nOR^3$, $CH_2CH_2Cl$ or $CH_2CF_3$;
$R^3$ is $C_1$-$C_4$ alkyl; and
n is 1 or 2;
provided that:
(1) when $R^1$ is $CH_2CH_2Cl$ or $CH_2CF_3$, then X is O; and
(2) when $R^2$ is $CH_2CH_2Cl$ or $CH_2CF_3$, then Y is O;
comprising
(a) contacting a dihydrohalide salt of the formula:

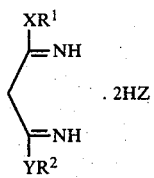

where X, Y, $R^1$ and $R^2$ are as defined above; and where Z is F, Cl or Br, with two mole equivalents of a base to produce a bisimidate; and
(b) contacting the bisimidate with cyanogen chloride to product a mixture of an N-cyanoimidate and a monohydrohalide bisimidate salt;
(c) isolating the N-cyanoimidate from the reaction mixture; and
(d) heating the resulting N-cyanoimidate at a temperature sufficient to induce ring closure.

2. The process of claim 1 wherein the base in step (a) is an alkali metal carbonate, alkali metal hydroxide, alkaline earth carbonate or alkaline earth hydroxide.

3. The process of claim 2 wherein the base is sodium or potassium carbonate.

4. The process of claim 1 wherein a solution of the dihydrohalide salt in methylene chloride is contacted with an aqueous solution of base at a temperature in the range of about $-10°$ to $50°$ C.

5. The process of claim 1 wherein a solution of the bisimidate in methylene chloride is contacted with cyanogen chloride at a temperature of about $0°$ to $80°$ C.

6. The process of claim 1 in which the monohydrohalide bisimidate salt is recycled by
(a) contacting the monohydrohalide bisimidate salt with one mole equivalent of a base to produce a bisimidate, and
(b) contacting the bisimidate with cyanogen chloride to produce an N-cyanoimidate.

7. A process for preparing a compound of the formula

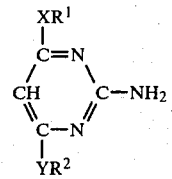

where
X and Y are independently oxygen or sulfur;
$R^1$ and $R^2$ are independently $C_1$-$C_4$ alkyl, $(CH_2)_nOR^3$, $CH_2CH_2Cl$ or $CH_2CF_3$;
$R^3$ is $C_1$-$C_4$ alkyl; and
n is 1 or 2;
provided that:
(i) when $R^1$ is $CH_2CH_2Cl$ or $CH_2CF_3$, then X is O, and
(ii) when $R^2$ is $CH_2CH_2Cl$ or $CH_2CF_3$, then Y is O;
comprising
(a) contacting a suspension of a dihydrohalide salt of the formula

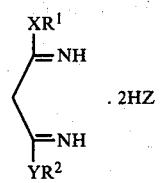

where X, Y, $R^1$ and $R^2$ are as defined above, and where Z is F, Cl or Br, in methylene chloride with two mole equivalents of sodium or potassium carbonate at a temperature in the range of about $-10°$ to $50°$ C. to produce a bisimidate;
(b) contacting a solution of the bisimidate in methylene chloride with cyanogen chloride at a temperature of about $0°$ to $80°$ C. to produce a mixture of an N-cyanoimidate and a monohydrohalide bisimidate salt;
(c) isolating the N-cyanoimidate;
(d) recycling the monohydrohalide bisimidate salt by
(i) contacting the monohydrohalide bisimidate salt with one mole equivalent of sodium or potassium carbonate under the conditions of step (a) to produce a bisimidate, and
(ii) contacting the bisimidate with cyanogen chloride under the conditions of step (b) and isolating the N-cyanoimidate formed thereby; and
(e) heating the resulting N-cyanoimidate at a temperature sufficient to induce ring closure.

* * * * *